United States Patent [19]
Hoffmann et al.

[11] Patent Number: 5,704,382
[45] Date of Patent: Jan. 6, 1998

[54] METHOD AND APPARATUS FOR CONTROLLING THE FLOW OF A LIQUID, AND VISCOSITY MEASURING METHOD THEREFOR

[75] Inventors: Amos Hoffmann; Mark Fishman, both of Ramat-Gan, Israel

[73] Assignee: Hoffmann & Hoffmann Electronic & Electro-Mechanical Engineering, Bnei Braq, Israel

[21] Appl. No.: 431,662

[22] Filed: May 2, 1995

[30] Foreign Application Priority Data

May 3, 1994 [IL] Israel ............................. 109523

[51] Int. Cl.$^6$ ............................................. G05D 7/06
[52] U.S. Cl. ................... 137/2; 73/54.29; 73/54.31; 137/487.5
[58] Field of Search ......................... 73/54.29, 54.31, 73/54.32, 54.34; 137/92, 487.5, 485, 486, 487, 492, 492.5, 2, 4

[56] References Cited

U.S. PATENT DOCUMENTS

| | | | |
|---|---|---|---|
| 2,280,947 | 4/1942 | Gulliksen | 73/54.29 |
| 3,079,787 | 3/1963 | Van Luik | 73/54.29 |
| 3,249,115 | 5/1966 | Young | 137/92 |
| 4,535,621 | 8/1985 | Gervais et al. | 73/54.35 X |

*Primary Examiner*—Stephen M. Hepperle
*Attorney, Agent, or Firm*—Ladas & Parry

[57] ABSTRACT

Method and apparatus for controlling the flow of a liquid from a supply pipe to a receiving device, to assure that only a preselected liquid is permitted to flow to the receiving device, by: feeding a sample quantity of the liquid from the supply pipe to a sampling receptacle while a main valve between the supply pipe and receiving device is closed; testing the liquid within the sampling receptacle by immersing a stirring device therein, rotating the stirring device by an electrical motor, measuring the load current of the electrical motor, and comparing the measured load current with a reference load current for the preselected liquid; and opening the main valve to permit the flow of the liquid from the supply pipe to the receiving device when the test results show a match of the measured load current with the reference value for the preselected liquid.

18 Claims, 4 Drawing Sheets

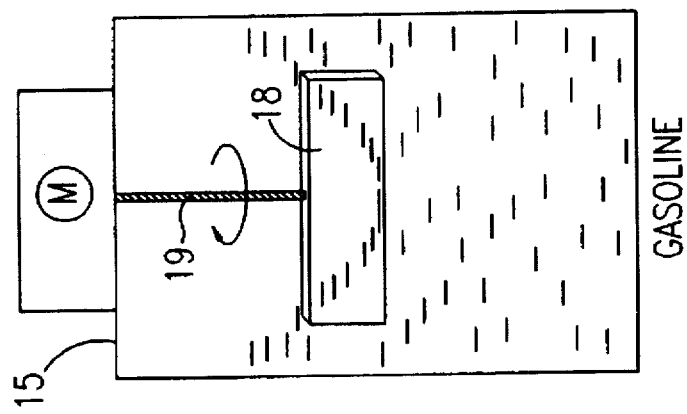
FIG. 2c GASOLINE
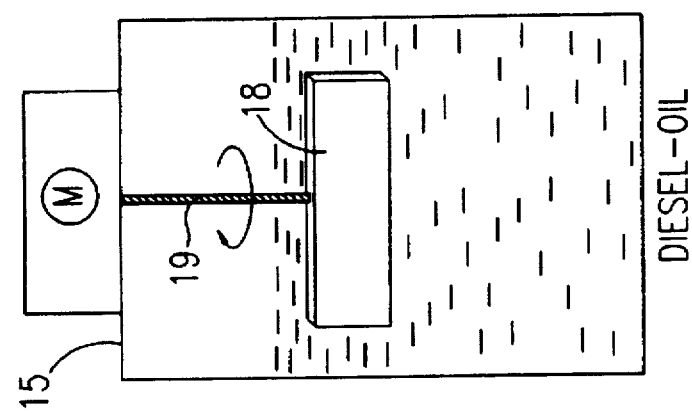
FIG. 2B DIESEL-OIL
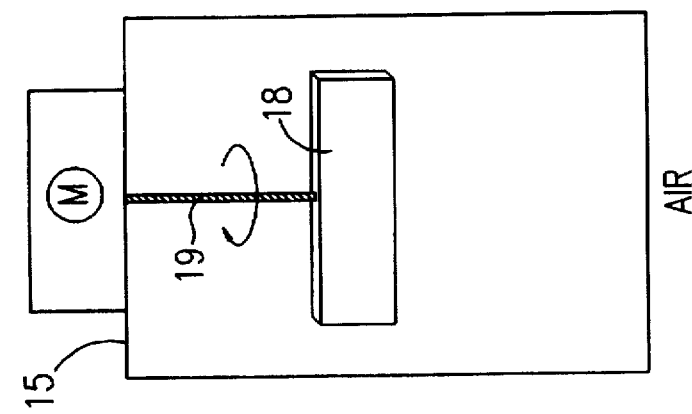
FIG. 2A AIR

METHOD AND APPARATUS FOR CONTROLLING THE FLOW OF A LIQUID, AND VISCOSITY MEASURING METHOD THEREFOR

FIELD AND BACKGROUND OF THE INVENTION

The present invention relates to a method and apparatus for controlling the flow of a liquid from a supply pipe to a receiving device, such as a storage tank, to assure that only a preselected liquid is permitted to flow to the receiving device. Such a method and apparatus are particularly useful for distinguishing between relatively heavy oil and relatively light gasoline, and is therefore described with respect to this case.

Distinguishing between an oil and a gasoline can be very critical to prevent damage to equipment and also to prevent dangerous conditions which could cause considerable damage to persons or property. For example, if a storage tank normally used for dispensing oil at a service station is accidentally filled with gasoline, an explosive condition could be created. Distinguishing between an oil and a gasoline can be done off-line in the laboratory without any difficulty, e.g., as by measuring the viscosity and/or specific gravity of the liquid. The difficulty, however, is when the test is to be made in real-time, on-line and automatically. Visual tests are not reliable because of the different colors oils and gasolines may take. Smell tests, which are sometimes made, are also not reliable, but more particularly, they do not lend themselves to real-time, on-line, automatic control.

At the present time oil and gasoline tanks generally include different types of connector arrangements to prevent a connector for a tank to receive one liquid from being connected to a feedline for the other liquid. However, such connector arrangements cannot entirely eliminate the possibility of mistakes; moreover, they are costly to incorporate, and costly also to change.

OBJECTS AND BRIEF SUMMARY OF THE INVENTION

An object of the present invention is to provide a novel method for controlling the flow of a liquid from a supply pipe to a receiving device, such as a storage tank, which method can be applied in real-time, on-line and automatically, to assure that only a preselected liquid is permitted to flow to the receiving device.

According to one aspect of the present invention, there is provided a method of controlling the flow of a liquid from a supply pipe to a receiving device, to assure that only a preselected liquid is permitted to flow to the receiving device, comprising: feeding a sample quantity of the liquid from the supply pipe to a sampling receptacle while a main valve between the supply pipe and receiving device is closed; testing the liquid within the sampling receptacle by immersing a stirring device therein, rotating the stirring device by an electrical motor, measuring the load current of the electrical motor, and comparing the measured load current with a reference load current for the preselected liquid; and opening the main valve to permit the flow of the liquid from the supply pipe to the receiving device when the test results are positive by a match (within preselected tolerances) of the measured load current with the reference value for the preselected liquid.

According to further features in the described preferred embodiment, the stirring device is immersed in the liquid such that the upper surface of the stirring device, when not rotated, is just below the liquid level and is covered by the liquid, and the rotation of the stirring device produces a vortex at the liquid level tending to cause the liquid to uncover the upper surface of the stirring device at its rotary axis.

As will be more particularly described below, the foregoing method may be used for automatically controlling a liquid supply line in a real-time, on-line manner, and automatically, to prevent a storage tank, intended to be filled with oil, from being accidentally filled with gasoline, and vice versa.

The invention also provides a novel method for measuring liquid viscosity, and also apparatus for controlling the flow of a liquid in accordance with the above method.

Further features and advantages of the invention will be apparent from the description below.

BRIEF DESCRIPTION OF THE DRAWINGS

The invention is herein described, by way of example only, with reference to the accompanying drawings, wherein:

FIGS. 2a, 2b and 2c more particularly illustrate a critical part of the apparatus of FIG. 1 in the manner in which it is used for testing liquids in accordance with the present invention;

DESCRIPTION OF A PREFERRED EMBODIMENT

Figure 1:
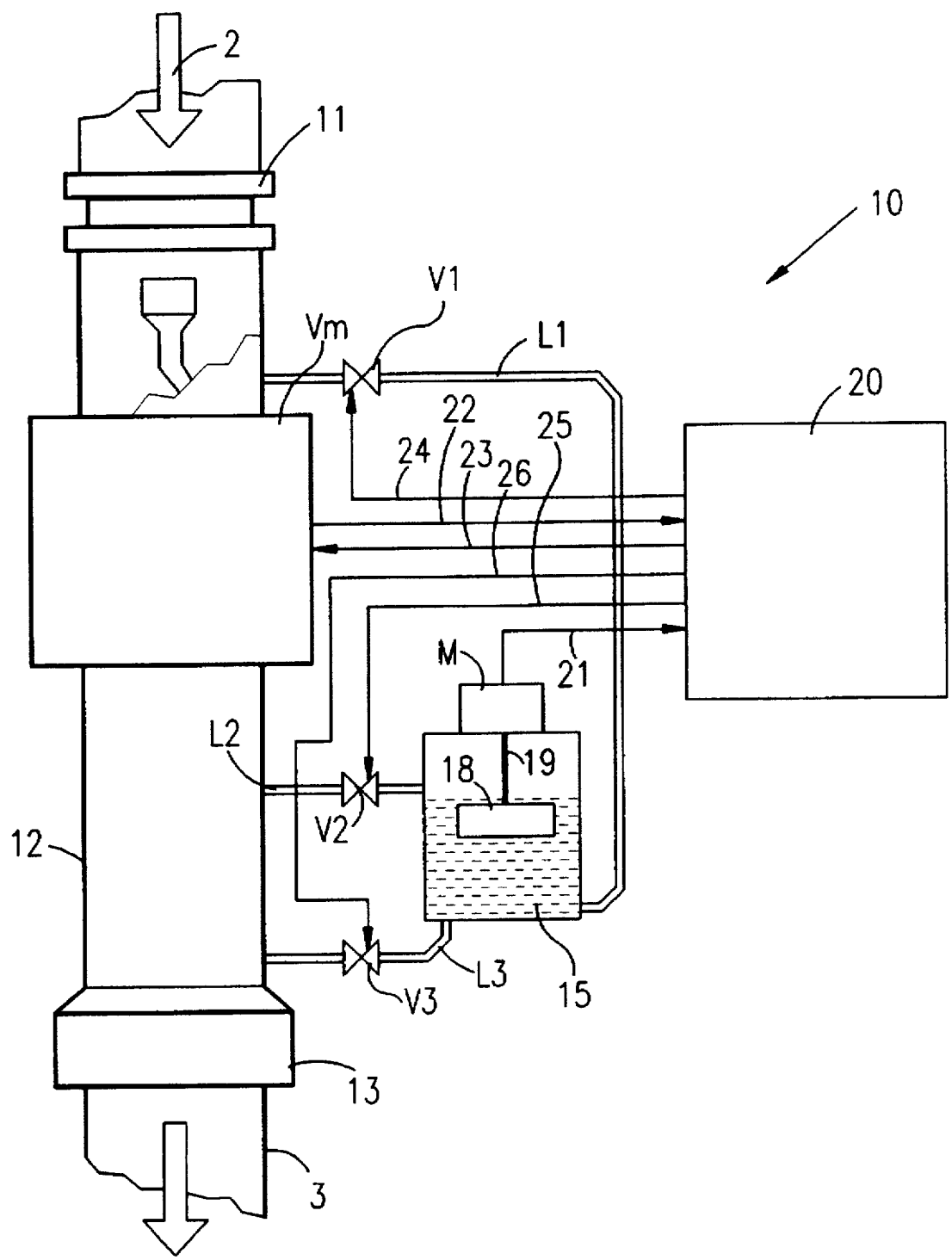
FIG. 1 is a schematical diagram illustrating one form of apparatus constructed in accordance with the present invention.

The apparatus illustrated in FIG. 1 is particularly useful for connecting a supply line 2, such as an oil or a gasoline line, to a feed line 3 leading to a storage tank (not shown) for the respective liquid. The apparatus illustrated in FIG. 1, and therein generally designated 10, is intended to be coupled between the supply line 2 and the feed line 3 for testing the liquid before it is fed via the feed line to the storage tank to make sure the liquid being fed is actually the liquid intended to be received by the storage tank. In the example described below, the storage tank may be for an oil or for a gasoline, in which case the apparatus would be used to make sure that the liquid being fed via the supply line 2 to an oil tank is actually an oil, since gasoline dispensed from an oil tank would create a potentially explosive situation, and that the liquid being fed to a gasolene tank is actually a gasolene and not an oil.

The apparatus 10 illustrated in FIG. 1 includes an inlet connector 11 for coupling to the supply line 2, a conduit 12 and an outlet connector 13 for coupling to the feed line 3 leading to the storage tank (not shown). The apparatus further includes a main shut-off valve $V_M$ which is normally closed, but which must be opened to pass the liquid from the supply line 2 to the feed line 3 leading to the storage tank.

The actual testing of the liquid is done in a sampling receptacle 15. This receptacle has an inlet line $L_1$ controlled by an inlet valve $V_1$ leading from conduit 12 to the bottom interior region of the receptacle. Receptacle 15 further includes an outlet line $L_2$ controlled by an outlet valve $V_2$ leading from a predetermined vertical level in the receptacle to the interior of conduit 12. A drain line $L_3$ is located at the bottom of receptacle 15 and includes a drain valve $V_3$ also leading into the interior of conduit 12.

A stirring device 18 is suspended by shaft 19 of motor M within receptacle 15 at a level just below that of the outlet line $L_2$. Stirring device 18 is thus located within the receptacle such that its upper surface is just below the liquid level within the receptacle. Motor M, which rotates the stirring device 18, is a DC motor and is supplied with a predetermined, regulated supply voltage. The load current drawn by the motor is fed to the supply voltage within an electronic control circuit 20.

Control circuit 20 includes a motor supply line 21 supplying current from the power supply within circuit 20 to motor M, which current is measured as described more particularly below. Circuit 20 further includes lines 22, 23 to the main shut-off valve $V_M$ for controlling (e.g., by limit switches, not shown) the open and closed positions of the valve. Circuit 20 further includes a control line 24 to inlet valve $V_1$, a control line 25 to outlet valve $V_2$, and a control line 26 to drain valve $V_3$.

The load current drawn by motor M, when rotating stirring device 18 within the liquid in the sampling receptacle 15, is used for identifying the liquid within the receptacle. In the application illustrated in FIG. 1, the liquid is tested and identified as being either an oil or a gasoline. The illustrated apparatus is first pre-calibrated for these two liquids; it is also pre-calibrated for air.

FIGS. 2a, 2b and 2c illustrate the stirring device 18 within the sampling receptacle 15 when it contains air, oil and gasoline, respectively. Stirring device 18 has the configuration of a rectangular prism, and a length greater than its width and thickness. It is rotated about the axis of motor shaft 19, which passes centrally through the stirring device.

As shown in FIG. 2a, stirring device 18 is rotated by motor M supplied with a predetermined voltage while receptacle 15 is empty of liquid, i.e., is filled with air. The load current so drawn by motor M via line 21 (FIG. 1) is measured, stored in the control circuit 20, and serves as a first (air) reference value.

FIG. 2b illustrates oil in receptacle 15 in which the stirring device 18 is rotated by motor M. The load current drawn by the motor is measured, stored in control circuit 20 (FIG. 1), and serves as a second (oil) reference value.

FIG. 2c illustrates gasoline in receptacle 15 in which the stirring device 18 rotated. The load current drawn by the motor M is measured, stored in control circuit 20 (FIG. 1), and serves as a third (gasoline) reference value.

In all three cases, the motor M is rotated when supplied with the same supply voltage, which is a regulated voltage from the control circuit 20. As one example, motor M may be a DC motor, and supplied with 6 volts. It will be appreciated that when the stirring device is rotated in air (FIG. 2a), the current drawn by the motor will be relatively low; when rotated in oil (FIG. 2b), it will be relatively high; and when rotated in gasoline (FIG. 2c), the current will be higher than that in air but below that in oil because of the lower viscosity of gasoline.

FIGS. 2b and 2c illustrate another feature of the invention. Thus, when the stirring device 18 is immersed such that its upper surface is just below the level of the liquid within receptacle 15 (i.e., just covered by the liquid), the rotation of the stirring device produces a vortex at the liquid level according to the viscosity (and probably also the specific gravity) of the liquid. In the case of gasoline (FIG. 2c), the vortex is quite deep and therefore tends to uncover or expose the upper surface of the stirring device at its rotary axis; this reduces the drag on the stirring device, and thereby the load current drawn by the motor. Where, the liquid is an oil (FIG. 2b), its higher viscosity (and specific gravity) produces a much shallower vortex so as to expose none or only a smaller portion of the upper surface of the stirring device, which thereby increases the load current drawn by the motor.

Accordingly, by thus immersing the stirring device so that its upper surface lies just below the liquid level, the vortex created by the rotation of the stirring device produces a sharper differentiation between liquids of lower viscosity and specific gravity such as gasoline, as compared to liquids of higher viscosity and specific gravity such as oil.

Before the apparatus is used, it is first calibrated by rotating stirring device 18 in air (FIG. 2a), in oil (FIG. 2b), and in gasoline (FIG. 2c), while measuring the load current in each case, to produce an air reference value, an oil reference value, and a gasoline reference value, respectively. To make the apparatus more universally applicable, the apparatus may be calibrated in this manner with respect to a plurality of oils and gasolines, and the average of each taken as the respective reference value. These values are stored in control circuit 20.

Figure 3:
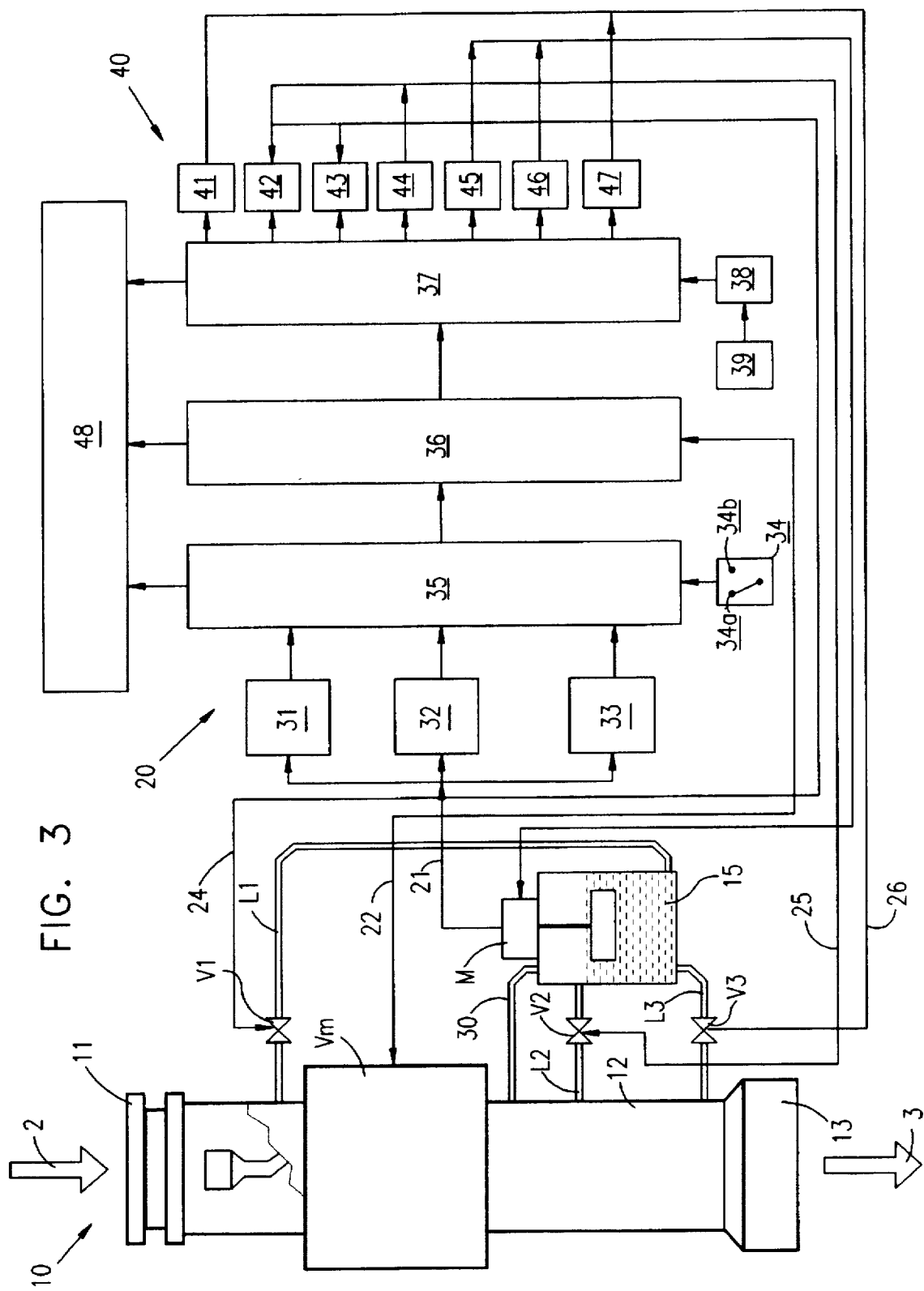
FIG. 3 is a schematical diagram illustrating more particulars of the apparatus of FIG. 1.

FIG. 3 illustrates more particulars of the control circuit 20. The apparatus itself is the same as described above with respect to FIG. 1, and therefore the same reference numerals have been used to identify the corresponding parts, except that whereas in FIG. 1 the sampling receptacle 15 was closed by an apertured top wall, the arrangement illustrated in FIG. 3 additionally includes an air vent 30 from the upper end of the sampling receptacle 15 leading into conduit 12.

As shown in FIG. 3, control circuit 20 includes three storage devices, 31, 32, 33 for storing the three reference values of load current produced as a result of calibrating the apparatus for air, oil and gasoline, respectively, as described above with respect to FIGS. 2a–2c. The system also includes a selector 34 which enables the user to preselect either oil or gasoline to be received in the storage tank via the outlet connector 13. This selection is inputted into a logic block 35 together with the load current produced by the motor M of the liquid under test, and together with the three reference values stored in storage devices, 31, 32 and 33. The logic block determines whether the load current of the tested liquid matches the reference value of the selected liquid; if so, logic block 35 outputs a signal to a driver circuit 36 which controls the main valve $V_M$.

The system illustrated in FIG. 3 is cyclically operated and includes a cycle counter 37 receiving outputs from the logic circuit 36 and controlled by a clock 38 enabled by a Start button 39. Cycle counter 37 controls a number of driver circuits, generally designated 40, as follows: driver 41 which closes drain valve $V_3$; driver 42 which opens inlet valve $V_1$; and outlet valve $V_2$; driver 43 which closes inlet valve $V_1$; driver 44 which closes outlet valve $V_2$; driver 45 which effects a Start test; driver 46 which effects a Stop test; and driver 47 which opens drain valve $V_3$.

The control circuit 20 illustrated in FIG. 3 further includes a display, generally designated 48, for displaying data pertaining to the operation of the apparatus and the test results produced.

Figure 4:
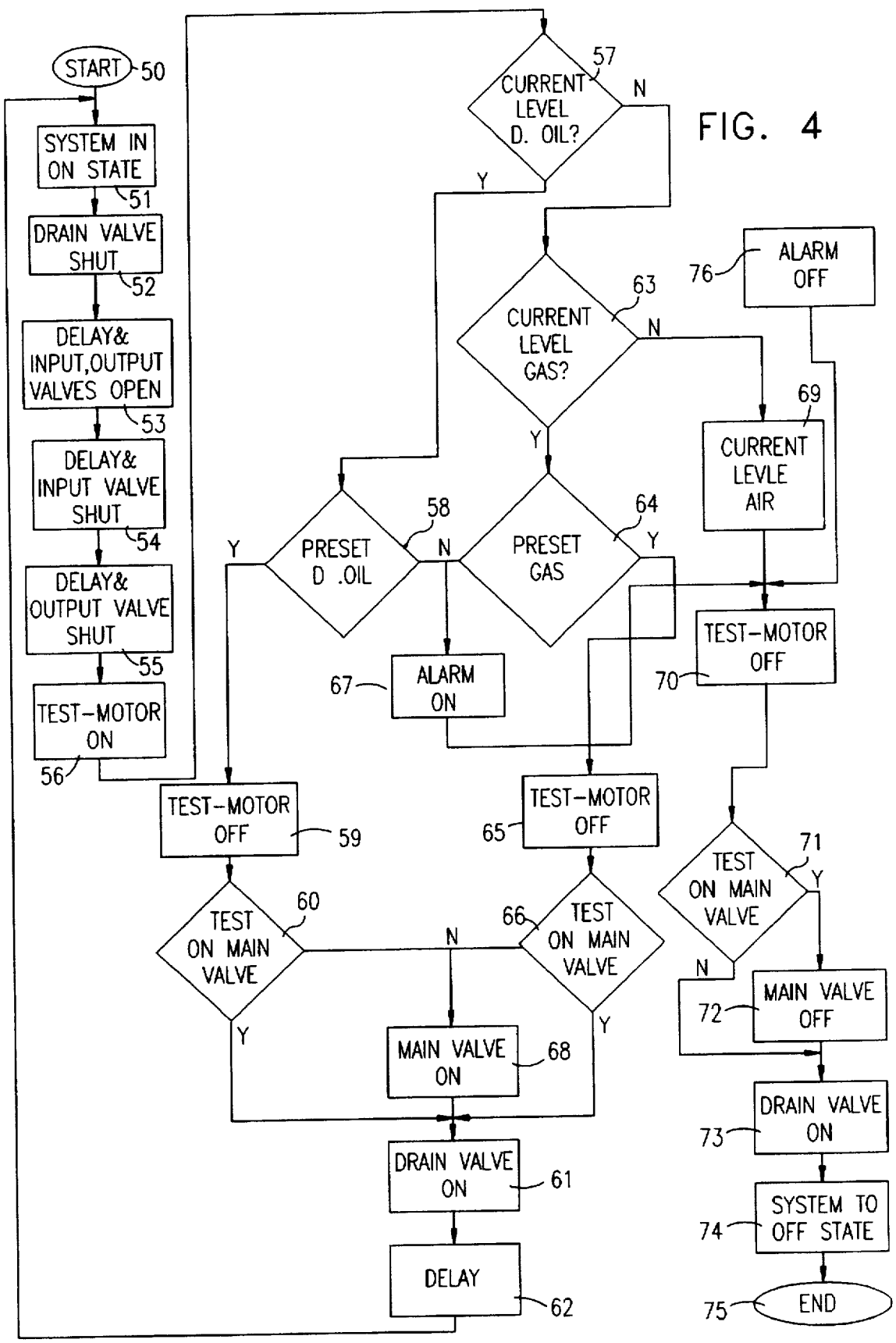
FIG. 4 is a flow chart illustrating the operation of the apparatus of FIG. 3.

One manner of operating the apparatus will now be described particularly with reference to the flow chart of FIG. 4.

Before using the described apparatus, the three reference values, namely the load current produced in motor M when its stirring device 18 is rotated in air (FIG. 2a), oil (FIG. 2b), and gasoline (FIG. 2c), are first stored in the three storage devices 31, 32, 33 (FIG. 3). Also, the selector 34 is manipulated to select oil (position 34a), or gasoline (position 34b), to be received within the tank connected to the feed line 3 (FIG. 1).

After the inlet connector 11 is connected to the supply line 2 (FIG. 1), and the outlet connector 13 is connected to the feed line 3, the system (FIG. 4) is turned on from the Start state (block 50) to the On state (block 51) by pressing Start button 39 which enables clock 38. This closes drain valve $V_3$ (block 52), and after a short delay, opens inlet valve $V_1$ and outlet valve $V_2$ (block 53). The liquid is thus inputted via inlet line $L_1$ and inlet valve $V_1$ into receptacle 15 to raise the liquid level above that of the outlet line $L_2$; valve $V_1$ is then closed (block 54), while valve $V_2$ remains open for a short time to permit the liquid to flow out of receptacle 15 until it reaches the level just above the upper surface of the stirring device 18, whereupon valve $V_2$ is closed (block 55). The motor M is then energized (block 56) to rotate the stirring device.

The load current drawn by the motor when rotating the stirring device 18 within receptacle 15 is checked to determine whether it matches the oil reference value (block 57). If it does, the system checks to see whether the selector 34 was preset for oil (block 58); if so, it deenergizes the motor M (block 59), and tests the state of the main valve $V_M$ (block 60). Since valve $V_M$ is then off, the system opens valve $W_M$ (block 68) to permit the liquid from the supply line to supply line to flow via the feed line 3 to the storage tank. In addition, the drain valve $V_3$ is opened to drain the liquid from the receptacle 15 (block 61), and after a delay (block 62), the system returns to Start to start a new cycle.

On the other hand, if gasoline had been preselected by the selector 34 (block 64), and the load current from the motor matched the gasoline reference value (block 63), the same sequence of operations are performed as described above, and as shown in blocks 61–66 and 68.

In either of the above sequences, if the liquid identified by the test does not match the liquid preselected in selector 34, the main valve $V_M$ is not open, but rather an alarm is actuated (block 67); this alarm is deactuated manually (block 76). In addition, if during either of the above sequences, testing of the main valve shows that it is not open (blocks 60, 66), the main valve $V_M$ is opened (block 68).

The foregoing cycles are repeated following a predetermined delay (block 62) of, e.g., 3–5 minutes between cycles, until air is sensed in receptacle 15 (block 69), thereby indicating that no further liquid is being fed from the supply. Motor M is then deenergized (block 70). If the main valve $V_M$ is still open (block 71), it is closed (block 72). Drain valve $V_3$ is opened (block 73); and the system goes to the Off state (block 74), whereupon the cycle is terminated (block 75).

For purposes of example, sampling receptacle 15 may be of cylindrical configuration having a diameter of 60 mm and a height of 90 mm; the inlet line $L_1$ may lead into receptacle 15 about 10–15 mm from its bottom; outlet line $L_2$ may lead out of the receptacle 35 mm from its top; stirring device 18 may be in the configuration of a rectangular prism having a length of 30 mm, a width of 10 mm, and a thickness of 0.5 mm; motor M may be a six-volt DC motor; and the rotational velocity of stirring device 18 may be about 2,400 rpm in air (FIG. 2a); it will, of course, be less in gasoline, and even less in oil.

While the invention has been described with respect to one preferred embodiment, it will be appreciated that this is set forth merely for purposes of example, and that many other variations, modifications and applications of the invention may be made.

We claim:

1. The method of controlling the flow of a liquid from a supply pipe to a receiving device, to assure that only a preselected liquid is permitted to flow to the receiving device, comprising:

feeding a sample quantity of the liquid from the supply pipe to a sampling receptacle while a main valve between the supply pipe and receiving device is closed;

testing the liquid within the sampling receptacle by immersing a stirring device therein, rotating said stirring device by an electrical motor, measuring the load current of the electrical motor, and comparing the measured load current with a reference load current for the preselected liquid;

and opening said main valve to permit the flow of the liquid from the supply pipe to the receiving device when the test results are positive by a match of the measured load current with the reference value for the preselected liquid.

2. The method according to claim 1, wherein said stirring device is immersed in the liquid such that the upper surface of the stirring device, when not rotated, is just below the liquid level and is covered by the liquid, and the rotation of the stirring device produces a vortex at the liquid level tending to cause the liquid to uncover the upper surface of the stirring device at its rotary axis.

3. The method according to claim 2, wherein said stirring device has a length greater than its width and thickness, and is rotated about an axis passing through its center.

4. The method according to claim 1, wherein said electrical motor is supplied with a predetermined supply voltage for said measured load current which voltage is the same as used for producing said reference load current.

5. The method according to claim 1, wherein, after said main valve has been opened to permit the flow of the liquid to said receiving device, subsequent samples of said liquid fed at periodic time intervals to said sampling receptacle are tested, and said main valve is maintained open so long as the test results with respect to said subsequent samples are positive.

6. The method according to claim 5, wherein the measured load current is also compared with an air reference value obtained by rotating the stirring device in air, and when found to match same, automatically closes said main valve.

7. The method according to claim 1, wherein the measured load current is compared with two liquid reference values obtained by rotating the stirring device in two different liquids, and automatically opens said main valve only when there is a match between the measured load current and the reference value of a preselected one of said two different liquids.

8. The method according to claim 7, wherein said two different liquids are oil and gasoline, respectively.

9. A method of measuring the viscosity of a liquid, comprising: immersing a stirring device in the liquid such that the upper surface of the stirring device is just below the liquid level;

rotating said stirring device by an electrical motor to a speed such as to produce a vortex at the liquid level tending to cause the liquid to uncover the upper surface of the stirring device at its rotatry axis;

and measuring the load current of the electrical motor.

10. The method according to claim 9, wherein said stirring device has a length greater than its width and thickness and is rotated about an axis passing through its center.

11. Apparatus for controlling the flow of a liqud from a supply pipe to a receiving device, to assure that only a preselected liquid is permitted to flow to the receiving device, comprising:

a normally closed main valve controlling the flow of the liquid from the supply pipe to the receiving device;

a sampling receptacle for receiving a sample of the liquid from the supply pipe;

a stirring device to be immersed in the liquid when received in the sampling receptacle;

an electrical motor for rotating said stirring device;

and a control circuit for testing a sample of the liquid in said sampling receptacle by measuring the load current of the electrical motor while rotating said stirring device, comparing the measured load current with a reference value of load current for the preselected liquid, and automatically opening said main valve to permit the flow of the liquid from the supply pipe to the receiving device only when the measured load current matches the reference value for the preselected liquid.

12. The apparatus according to claim 11, wherein said stirring device is supported so as to be immersed in the liquid sample when received in the receptacle such that the upper surface of the stirring device, when not rotated, is just below the liquid level and is covered by the liquid, and the rotation of the stirring device within the liquid sample produces a vortex at the liquid level tending to cause the liquid to uncover the upper surface of the stirring device at its rotary axis.

13. The apparatus according to claim 12, wherein said stirring device has a length greater than its width and thickness, and is rotated about an axis passing through its center.

14. The apparatus according to claim 13, wherein said stirring device is in the configuration of a rectangular prism.

15. The apparatus according to claim 11, wherein said control circuit includes means for supplying the electrical motor with a predetermined supply voltage when rotating the stirring device in said sample quantity of liquid to produce said measured load current which predetermined supply voltage is the same as when producing said reference load current.

16. The apparatus according to claim 11, wherein said control circuit also periodically tests additional samples of said liquid received in said sampling receptacle, compares the measured load current with an air reference value obtained by rotating the stirring device in air, and automatically closes said main valve when a match is found between said measured load current and said air reference value.

17. The apparatus according to claim 11, wherein said control circuit includes a storage device for storing the reference values of a plurality of different liquids obtained by rotating said stirring device within the respective liquids; and a selector for selecting one of said liquids; said control circuit being effective to open said main valve only when said measured load current is found to match the reference value of said selected liquid.

18. The apparatus according to claim 11, wherein said sampling receptacle includes an inlet line from the supply pipe into the sampling receptacle, an inlet valve in said inlet line, an outlet line just above the upper surface of the stirring device, and an outlet valve in said outlet line;

and wherein said control circuit is effective to open said inlet valve and to close said outlet valve when inletting the liquid into the sampling receptacle to a level above said outlet line, to close said inlet valve, and after a predetermined time delay sufficient for the liquid to lower to that of said outlet line, to close said outlet valve, and then to actuate said electrical motor to rotate the stirring device.

\* \* \* \* \*